United States Patent
Prabhakaran et al.

(10) Patent No.: US 11,957,744 B2
(45) Date of Patent: Apr. 16, 2024

(54) MONOVALENT VACCINE FORMULATION AND A METHOD FOR PREPARATION THEREOF

(71) Applicant: AIMST UNIVERSITY, Bedong Kedah (MY)

(72) Inventors: Guruswamy Prabhakaran, Bedong (MY); Manickam Ravichandran, Bedong (MY); Kurunathan A/L Sinniah, Bedong (MY); Yean Yean Chan, Penang (MY)

(73) Assignee: AIMST UNIVERSITY, Bedong (MY)

( * ) Notice: Subject to any disclaimer, the term of this patent is extended or adjusted under 35 U.S.C. 154(b) by 401 days.

(21) Appl. No.: 16/960,865

(22) PCT Filed: Dec. 26, 2018

(86) PCT No.: PCT/MY2018/050098
§ 371 (c)(1),
(2) Date: Jul. 8, 2020

(87) PCT Pub. No.: WO2019/139468
PCT Pub. Date: Jul. 18, 2019

(65) Prior Publication Data
US 2022/0175905 A1    Jun. 9, 2022

(30) Foreign Application Priority Data
Jan. 9, 2018  (MY) .......................... PI 2018700106

(51) Int. Cl.
*A01N 63/00* (2020.01)
*A61K 39/02* (2006.01)
*A61P 31/04* (2006.01)
*A61K 39/00* (2006.01)

(52) U.S. Cl.
CPC ............ *A61K 39/107* (2013.01); *A61P 31/04* (2018.01); *A61K 2039/522* (2013.01)

(58) Field of Classification Search
CPC .................................................. A61K 39/107
See application file for complete search history.

(56) References Cited

U.S. PATENT DOCUMENTS

| 4,169,886 A | 10/1979 | Hertman et al. |
| 2006/0099229 A1 | 5/2006 | Ravichandran |

FOREIGN PATENT DOCUMENTS

| WO | 2002020059 A2 | 3/2002 |
| WO | 2001068829 A2 | 10/2011 |

OTHER PUBLICATIONS

Ravichandran, M., et al., "Construction and evaluation of a 0139 Vibrio Colerae Vaccine candidate based on a hemA gene mutation", May 2006, Vaccine, vol. 24, pp. 3750-3761.
Chan, M., et al. "Construction and characterization of an auxotrophic ctxA mutant of 0139 vibrio colerae" Nov. 2010, Microbial Pathogenesis, vol. 40, pp. 211-216.
Chandrika, M., et al."Construction and Histopathological Characterization of Multiple Virulent Genes Mutant of V. cholerae: To Understand the Enteropathogenesis of Cholerae" Dec. 2008, International Journal of Infectious Disease, vol. 12.
Tacket, C.O., et al., "Initial Clinical Studies of CVD 112 Vibrio cholerae 0139 Live Oral Vaccine: Safety and Efficacy against Experimental Challenge", Sep. 1995, The Journal of Infectious Diseases, vol. 172.
Kaper, J.B., et al.. "Attenuated Vibrio cholerae strains as live oral cholera vaccines and vectors", 2004, New Generation Vaccines, 3rd Edition.
Coster, T.S. et al., "Safety, immunogenicity, and efficacy of live attenuated Vibrio cholerae 0139 vaccine prototype" Apr. 1995, The Lancet, vol. 345.
Xian, T.W., "Repeated dose toxicity evaluation of a cold chain-free, live, attenuated oral cholera vaccine in Sprague Dawley rats" Jan. 2019.

*Primary Examiner* — Albert M Navarro
(74) *Attorney, Agent, or Firm* — Maschoff Brennan

(57) ABSTRACT

The present invention discloses a vaccine formulation in accordance with an illustrative embodiment. The formulation including a live attenuated cholera vaccine strain VCUSM14P; a vaccine medium having starch, cellulose, dextrose, and yeast extract; and a phosphate buffer saline.

5 Claims, 3 Drawing Sheets

Specification includes a Sequence Listing.

Table 01

| | Primer | Sequence 5' --- 3' | $T_A$°C | Function |
|---|---|---|---|---|
| Set A | KanFse-2F | AGCGGCCGGCCGCTTACATGGCGATAGCTAG | 58 | Screening of aphA in mutant *V.cholerae strains* |
| | KanFse-R | ATAGGCCGGCCTCAGAAGAACTCGTCAAGAA | | |
| Set B | MctxA112MS-F | TACAGTCCTCATCCAGATCAG | 65 | Mutagenic screening primer for 112th amino acid codon of ctxA |
| | ctxBCDS-R | AATTGCCATACTAATTGCGGC | | |
| Set C | MctxA112WS-F | TACAGTCCTCATCCAGATGAA | 65 | To detect *Vibrio cholerae* wild type strain |
| | ctxBCDS-R | AATTGCCATACTAATTGCGGC | | |

Figure 3

MONOVALENT VACCINE FORMULATION AND A METHOD FOR PREPARATION THEREOF

The sequence listing disclosed herein is included in a text file having the name "A4126-10034U01-Sequence_Listing," created on Jan. 20, 2021, having a size of 1,723 bytes. The foregoing text file is incorporated herein by reference.

FIELD OF INVENTION

The present invention relates generally to a vaccine formulation and a method for preparation thereof. More particularly, the present invention relates to a monovalent vaccine formulation for treating against O139 *V. cholerae*. The formulation is a cold chain free and long-lasting, and the present invention also discloses a method for preparation thereof.

BACKGROUND OF THE INVENTION

*Vibrio cholerae* is a Gram-negative, comma-shaped bacterium. The bacterium's natural habitat is brackish or saltwater. Some strains of *V. cholerae* cause the disease cholera. Cholera can be endemic, epidemic, or pandemic. Despite all the major advances in research, the condition still remains a challenge to the modern medical world. Although the disease may be asymptomatic or mild, severe cholera can cause dehydration and death within hours of onset. Cholera, the diarrheal disease causes epidemics across the globe with an estimated 4.3 million cases and 129064 deaths annually in 47 countries.

The bacterium inhabits aquatic ecosystems as well as in host intestinal tract. In aquatic environment, both toxigenic and nontoxigenic *V. cholerae* strains survive year-round. The toxigenic strains typically through the ingestion of contaminated water or food enter the human host, colonize the small intestine, multiply and produce the cholera toxin, which causes acute diarrhoeal disease. In endemic areas, large-scale oral vaccine campaigns are organized every year worldwide. However, there are operational challenges in implementing the cholera vaccination campaign in the developing countries with the existing WHO licensed oral cholera vaccines, for example, Dukoral®, Shanchol® and ORC-VAX®. Such vaccines are based on whole-cell, killed *Vibrio cholerae* O1 and O139 serogroups. Such vaccines are safe and induce adequate short-term protection. However, the vaccines demand cold-chain supply (2-8° C.) to ensure the potency of vaccines from manufacturing to the immunization site, resulting in an increase of the vaccination cost by 14-20%. In addition, such vaccines have to be consumed repetitively, leading to high cost. As an alternative, cholera vaccine based on live attenuated strains mimic natural infection, strongly immunogenic, eliminates the repetitive dosing. Besides, when compared to the highly purified subunit and whole-cell, killed vaccines, it does not require sophisticated downstream processing and is relatively low cost to produce. The various growth-inhibiting stresses in the environment such as deprivation of nutrients, fluctuations in temperature, salinity and oxygen level elicit stringent responses in *V. cholerae* involving modulation of expression of several genes to mediate their adaptation, persistence, dissemination and transmission of cholera.

For example, European patent publication EP1650315B1 and US patent publication U.S. Pat. No. 7,838,016B2 disclose *Vibrio cholerae* strains VCUSM1 and VCUSM4, method of producing same, and vaccine derivatives thereof. The method involves mutation in the hemAgene of both the strains VCUSM1 and VCUSM4 rendering the *Vibrio cholerae* incapable of synthesizing aminolevulinic acid (ALA) de novo. Such vaccines showed potential as a new non-toxic vaccine candidate toxic against O139 *V. cholerae* capable of eliciting high antibody titers and protective immune responses. However, similar to other cholera vaccines, the formulations made with live attenuated VCUSM1 and VCUSM4 strains are also sensitive to heat and require the cold-chain supply.

In another example, US patent publication U.S. Pat. No. 4,169,886A relates to a live vaccine against *Pasteurellamultocida*, for application of poultry by injection, per os or as aerosol, containing an attenuated non-virulent genetically stable strain of *Pasteurellamultocida*, to a process for producing an attenuated genetically stable non-virulent strain of *Pasteurellamultocida*, which comprises cultivating a virulent field strain, selecting after 18 hours at 37° C. However, the vaccine is mainly for poultry and is cold chain dependent.

Therefore, it is inevitable to develop a thermo-stable live attenuated cholera vaccine which can be stored at room temperature to increase its outreach to global immunization program. Like other microorganisms, *Vibrio cholerae* bacterial strains are also master adopters for their survivability in the hostile natural environment. Hence, by unrevealing their adaptation/survival mechanism in the natural conditions, we can mimic the similar conditions in formulating the vaccine candidate to make its storage at cold chain free conditions to serve the bottom billion at the last mile.

Hence, there exists a need for developing a vaccine formulation which can be cold chain free avoiding repetitive dosing, leading to lower cost and longer lifethereof.

SUMMARY OF THE INVENTION

The present invention has been made in the view of the above problems, and the present invention discloses a monovalent vaccine formulation against O139 *V. cholerae* in accordance with an illustrative embodiment. The formulation including a live attenuated cholera vaccine strain VCUSM14P; a vaccine medium having starch, cellulose, dextrose, and yeast extract; and a phosphate buffer saline.

In another embodiment, the present invention discloses use of a monovalent vaccine formulation. The formulation includes a live attenuated cholera vaccine strain VCUSM14P grown in a vaccine medium having starch, cellulose, dextrose, and yeast extract in a phosphate buffer saline. The formulation is configured for treating WT *V. cholerae* O139.

In another embodiment, the present invention discloses use of a monovalent vaccine formulation. The formulation including a live attenuated cholera vaccine strain VCUSM14P grown in a vaccine medium having starch in the range of 1%-5%, at least 0.3% cellulose, at least 20% dextrose and at least 0.5% yeast extract in a 1000 mL of phosphate buffer saline (pH 7.2). The formulation is configured for treating WT *V. cholerae* O139.

In yet another embodiment, the present invention discloses a method for preparing a monovalent vaccine formulation against O139. The method includes culturing of live attenuated bacterial cells of strain VCUSM14P in a vaccine growth medium. The method further includes recovering the bacterial cells from the culture. Finally, the recovered bacterial cells are suspended in a phosphate buffer saline.

BRIEF DESCRIPTION OF DRAWINGS

Other objects, features, and advantages of the invention will be apparent from the following description when read with reference to the accompanying drawings. In the drawings, wherein like reference numerals denote corresponding parts throughout the several views:

Figures

FIG. 3 includes a table (referred to herein as Table 01) which represents a list of primers along with sequences thereof, along with annealing temperature and functions used for developing a monovalent vaccine formulation against O139 challenge, in accordance with an illustrative embodiment of a present invention.

DETAILED DESCRIPTION OF THE PREFERRED EMBODIMENTS

Figure 1:
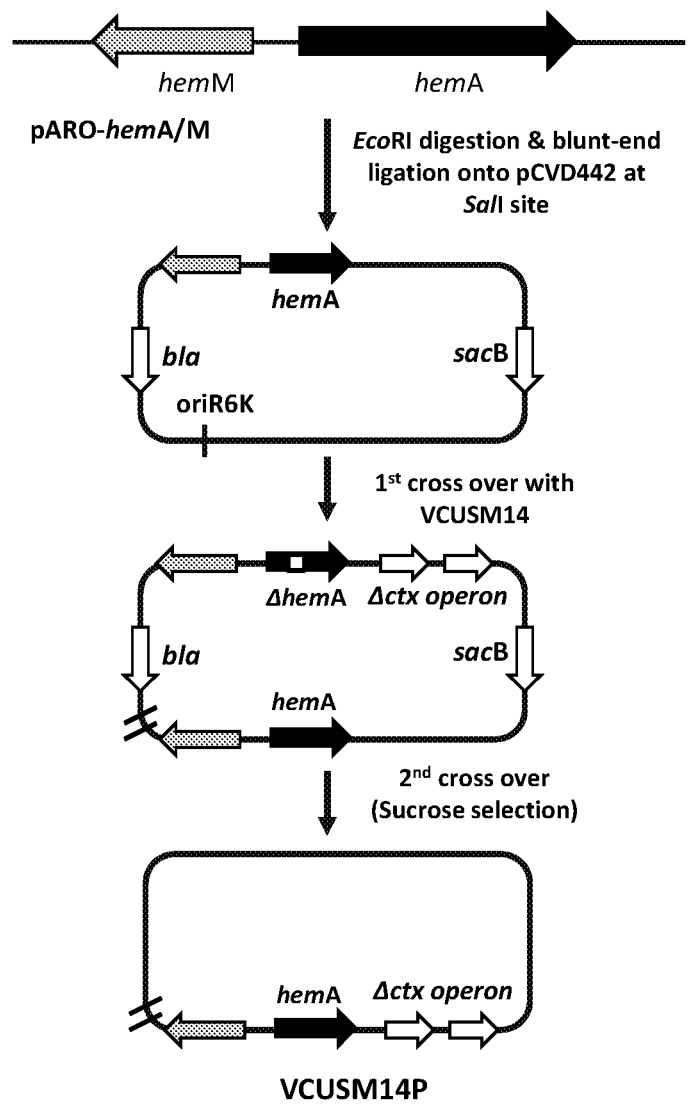
FIG. 1 illustrates a schematic of construction of a live attenuated cholera vaccine strain VCUSM14P, in accordance with an illustrative embodiment of a present invention.

Reference will now be made in detail to the preferred embodiments of the present invention, examples of which are illustrated in the accompanying drawings.

In the following detailed description, numerous specific details are set forth in order to provide a thorough understanding of the invention. However, it will be understood by those or ordinary skill in the art that the invention may be practiced without these specific details. In other instances, well known methods, procedures and/or components have not been described in detail so as not to obscure the invention.

The invention will be more clearly understood from the following description of the methods thereof, given by way of example only with reference to the accompanying drawings. In the descriptions that follow, like numerals represent like elements in all figures. For example, where the numeral (2) is used to refer to a particular element in one figure, the numeral (2) appearing in any other figure refers to the same element.

Cholera is an acute, diarrheal illness caused by infection of the intestine with the bacterium *Vibrio cholerae*. An estimated 3-5 million cases and over 100,000 deaths occur each year around the world. The infection is often mild or without symptoms, but can sometimes be severe. Approximately one in 10 (5-10%) infected persons can have severe disease characterized by profuse watery diarrhea, vomiting, and leg cramps. In such people, rapid loss of body fluids leads to dehydration and shock. Without treatment, death can occur within hours.

Currently, there is a number of vaccine formulations developed to get rid of the diarrheal illness. Such vaccines are whole-killed or live attenuated *Vibrio cholera* based. Both types of the vaccines have potential as vaccine candidate against O139 *V. cholerae*. Such vaccines have capability of eliciting high antibody titers and protective immune responses. However, there are certain challenges with the vaccines. For example, the vaccines are cold chain dependent, therefore requiring repetitive dosage thereof. Such characteristics thereof lead to higher cost and also short lasting.

Therefore, the present invention discloses a live attenuated cholera vaccine formulation which is cold chain free leading to a single dosage thereof and hence lowers the cost involved. In some embodiments, the formulation has stability at room temperature, therefore long lasting. In some embodiments, the present invention discloses a method for preparing the live attenuated cholera vaccine formulation. The various growth-inhibiting stresses in the environment such as deprivation of nutrients, fluctuations in temperature, salinity and oxygen level elicit stringent responses in *V. cholerae* involving modulation of expression of several genes to mediate their adaptation, persistence, dissemination and transmission of cholera. Therefore such adoptive traits of *V. cholerae* can be leveraged at an in-vitro condition that best mimic the environmental stress conditions for the extended storage period of live attenuated cholera vaccine strain at ambient temperature.

In an embodiment, the present invention discloses a monovalent vaccine formulation against O139. The formulation includes a live attenuated cholera vaccine strain grown in a vaccine medium. In some embodiments, the vaccine strain is VCUSM14P. VCUSM14P is an amino-leuvulinic acid (ALA) prototroph and non-toxigenic strain constructed against O139 serogroup of *V. cholerae*. A protocol for constructing the ALA prototroph, VCUSM14P is depicted in FIG. 1. As shown in FIG. 1, the wild type hemA/M genes are excised from pARO-hemA/M through EcoRI restriction enzyme digestion. The 2.18 kb fragment containing the 5' flanking hemA/M are then blunted with T4 DNA polymerase and cloned into a linearized suicide vector, pCVD442, at the SalI restriction enzyme site to produce pCVD-hemA/M. The successful cloning of pCVD-hemA/M confirmed by PCR using VHF (5'-GAC CTG TGA TGT AAA GGA AC-3') SEQ ID NO: 1 and VHR (5'-CTT CAT AGC GCT CAA CAA GG-3') SEQ ID NO: 2 primers. The pCVD-hemA/M containing intact hemA/M gene is conjugationally transferred from the *E. coli* host, BW 20767 λ-pir, to VCUSM14 strain. The resulting merodiploids possessing the suicide vector construct, pCVD-hemA/M, integrated into VCUSM14 chromosome as a result of the first crossover event, are selected on LB agar containing ampicillin and polymyxin B. The prototrophic strains with wild type hemA/Mgene are selected using modified LB medium containing 15% sucrose. A strain that is sensitive to ampicillin, resistant to both polymyxin B and sucrose and shows an absence of ALA auxotrophy is selected and designated as VCUSM14P. Various primer sequences along with respective functions have been enlisted in Table 01.

Experiment

The sub culture of live attenuated cholera vaccine (VCUSM14P) is maintained on Sigma-Aldrich LB agar without any antibiotics and routinely propagated at 37° C. in LB broth (LB; 10 g/l tryptone, 5 g/l yeast extract, and 5 g/l sodium chloride). Wild Type (WT) *V. cholerae* 0319 Bengal strain is maintained on Oxoid Nutrient Agar composed of Bacto peptone 10 g/l, Lab lemco powder 10 g/l, sodium chloride 5 g/l and plain agar 15 g/l supplemented with polymyxin 0.75 g/ml. Thiosulfate citrate bile salts sucrose (TCBS) agar enumerates the VCUSM14P in intestinal colonization studies. The stock culture of strains is stored in 15% glycerol with brain heart infusion broth (BHIB, Difco) at −80° C. until used.

In some embodiments, the strain VCUSM14P is grown in a vaccine medium. The medium further comprising starch (3.25-6.75%), cellulose (2.50-4%), dextrose (18.25-24.50%), yeast extract (0.01-0.05%), and NaCl (0.05-0.15%) in a 1000 mL of phosphate buffer saline at pH 7.2±0.2.

In the above embodiments, the formulations mediate antibody and cytotoxic T cells.

In some embodiments, the present invention discloses a method for preparing the cholera vaccine formulation. The sequence of the steps of the method described hereinafter is exemplary in nature to understand the skill in the art. The method includes culturing of live attenuated bacterial cells of strain VCUSM14P in a vaccine growth medium. The method further includes recovering the bacterial cells from the culture. Finally, the recovered bacterial cells are suspended in a phosphate buffer saline.

Experiment

A single colony of VCUSM14P from stock culture purity plates is inoculated in 100 ml Erlenmeyer flask containing 20 ml LB broth and incubated at 37° C. for 24 hours in an orbital shaker set at 250 rpm. Bacterial growth is monitored using a spectrophotometer for OD measurements at 600 nm. Such culture inoculates 200 ml of fresh LB broth in a 1000 ml Erlenmeyer flask and incubates at the same conditions for 4 hours. Further, 4 hours culture inoculates 2 L vaccine growth medium.

In a 5 L bench top fermenter (BIOSTAT A Plus, Sartorius, Germany) the vaccine strain (VCUSM14P) is cultivated in the vaccine growth medium (LB broth supplemented with 1% starch and 0.3% cellulose) in a laboratory fermenter at 37° C., 0.6 vvm aeration and 150 rpm agitation for 48 hours. The cells are recovered by centrifugation at 10,000 rpm for 20 min at 4° C. The recovered bacterial cells are suspended in 200 ml of phosphate buffer saline (pH 7.2).

A sterile solution of excipients is prepared in 1000 ml of phosphate buffer saline (pH 7.2) supplemented with 5% starch, 1.5% cellulose, 20% dextrose and 0.05% yeast extract. The Live Attenuated Cholera Vaccine (LACV) formulation is done by aseptically mixing together 200 ml of the saline suspension of bacterial cells ($6\times10^8$ CFU/ml) and 800 ml of the sterile solution of excipients. The formulation undergoes homogenously mixing and incubation at 37° C. for 48 h. After 48 hours, 5 ml aliquots of vaccine formulation is dispensed aseptically in 10 ml glass vials, closed with rubber stopper and stored at room temperature (25±2° C.).

Further, the storage stability of the formulation undergoes evaluation for its purity, potency and viability. The evaluation can be done by phenotypic and genotypic methods over an extended storage period of 180 days at 25° C.±2° C. and 60%±5% humidity.

The viability of the strain in the formulation is 2 logs lower after 180 days of storage as compared to its storage at room temperature (25° C.±2° C.) ie; $6\times10^8$ CFU/ml and the reduction of colonies may be attributed to the high humidity.

To identify the intact VCUSM14P culture in the formulation after 180 days of storage at 25° C.±2° C. and 60%±5%, PCR can be performed by using two different primer sets. PCR and gel electrophoresis ascertain the genetic purity of VCUSM14P culture in the cold chain free formulation.

The first PCR reaction is the Mctx reaction using ctxA112MS-F and ctxBCDS-R primer for the detection of the presence of the mutated ctxA gene in the samples to verify that the mutated ctxA gene does not revert back to the toxigenic form. All the samples containing culture in the formulations as well as the positive control which is the VCUSM14P strain from the glycerol stock (unformulated strain) have shown the band at 700 bps region, while no band is observed in the negative control column. Such a result indicates that mutated ctxA gene is present in the culture and it is free from contamination.

The second PCR reaction includes KanFse reaction. The KanFse reaction involves KanFse-2F and KanFse-R primers to detect the presence of the genetic marker inserted into VCUSM14P, which is the truncated aphA gene. aphA gene is a kanamycin resistance gene. All the samples containing culture in the formulations as well as the positive control show the band at 500 bps region. The presence of aphA gene in the formulation culture indicates it is a VCUSM14P strain which comparable to the positive control (VCUSM14P from glycerol stock (unformulated) strain.

During the extended storage at 25° C.±2° C. and 60%±5% humidity, the bacterial colonies from the LACV formulation are isolated periodically and streaked on TCBS agar. The colonies of VCUSM14P in formulation show 2-4 mm in diameter flat yellow colonies with opaque centers on TCBS agar. Gram staining shows the presence of Gram negative "comma" (curved rod) shaped cells under a light microscope. Besides, a series of biochemical tests are performed with HiVibrio™ identification kit to validate the identity of *Vibrio cholerae*(VCUSM14P) strain. All the above test results confirm the presence of a pure culture of VCUSM14P strain in the LACV formulation.

Since colonization is critical for elicitation of the immune response, the LACV formulation is examined for its colonization in the infant mouse model. The LACV formulation stored at 25° C.±2° C. and 60%±5% humidity for 180 days undergoes evaluation for its colonization potential in infant mouse model. In such an assay, $7\times10^7$ CFU/ml of VCUSM14P is recovered after inoculation of 5×106 CFU/ml of formulation. The colonization potential of formulated VCUSM14P has one log higher recovery rate.

Experiment

Reactogenicity studies in rabbit can be carried out. In ligated ideal loop assay, loops injected with $10^4$, $10^5$ and $10^6$ CFU of LACV formulation can be recorded with significant decrease in fluid accumulation (0.2 Fluid Accumulation Ratio). Whereas, loops injected with $10^4$, $10^5$ and $10^6$ CFU of WT *Vibrio cholerae* O139 record with 4 fold increase in fluid accumulation (0.8 FluidAccumulation Ratio) and show the presence of hemorrhage. The LACV formulation is non-reactogenic at doses $10^4$-$10^6$ in rabbit ideal loop model.

Figure 2A:
FIG. 2A shows an image of unvaccinated rabbit.
Figure 2B:
FIG. 2B shows an image of a rabbit vaccinated with an oral unformulated monovalent vaccine formulation.
Figure 2C:
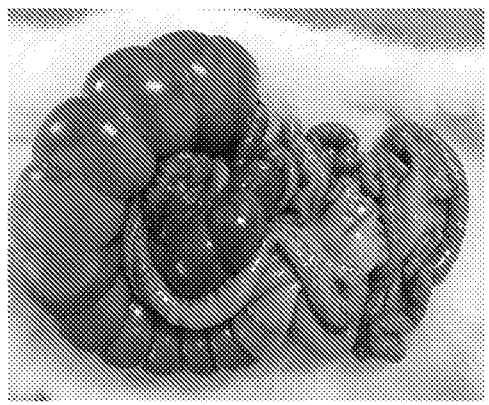
FIG. 2C shows an image of a rabbit vaccinated with an oral formulated monovalent vaccine formulation, in accordance with the illustrative embodiment of the present invention.

The vaccine formulation undergoes further evaluation for its protective capability in rabbit models. The protective capability can be determined using Reversible Intestinal Tie Adult Rabbit Diarrhoea (RITARD) model.RITARD Assay is performed on normal rabbits and rabbits immunized with LACV formulation by challenging with $10^9$ CFU/ml WT *Vibrio cholerae* O139. Rabbits immunized with 10 ml of LACV formulation ($5\times10^6$ CFU/ml) do not show any sign of diarrhea or mortality up to 5 days at observation, whereas 100% mortality is observed on normal rabbits after 18 hours in RITARD model as shown in FIGS. 2A, 2B, and 2C. 2 male unvaccinated rabbits each of 3 kg are challenged with $1\times10^9$ CFU/ml WT *V. cholerae* O139 Bengal strain. After $18^{th}$ hour, fluid accumulation in small intestine thereof is found as shown in FIG. 2A. 3 male rabbits each of 3.1 kg vaccinated with an oral 10 mL of unformulated VCUSMP14P show no signs of diarrhea after $6^{th}$ day of vaccination. As shown in FIG. 2B, no fluid accumulates in small intestine thereof. Similarly, when 3 male rabbits each of 3.2 kg undergo vaccination with an oral 10 mL of formulated VCUSMP14P, the rabbits show no signs of diarrhea after $6^{th}$ day of vaccination. As shown in FIG. 2C, no fluid accumulates in small intestine thereof.

The immune response of rabbits immunized with LACV formulation is evaluated by measuring anti-CT IgG antibodies. The anti-CT IgGis induced in rabbits vaccinated with LACV formulation when compared to pre-immune sera. An increase in IgG antibody response start at week 2 with increase of 6 fold and highest IgG response is recorded at week 4 with 17 fold in rabbits vaccinated with the LACV formulation.

Therefore, the LACV formulations are cold chain free, stable at 25° C.±2° C. and 60%±5% humidity for 180 days, non-reactogenic and immunogenic in vivo, and protect animals from lethal WT *V. cholerae* O139 challenge.

While the preferred embodiment of the present invention and its advantages has been disclosed in the above Detailed Description, the invention is not limited there to but only by the scope of the appended claim.

As will be readily apparent to those skilled in the art, the present invention may easily be produced in other specific forms without departing from its essential characteristics. The present embodiments are, therefore, to be considered as merely illustrative and not restrictive, the scope of the invention being indicated by the claims rather than the foregoing description, and all changes which come within therefore intended to be embraced therein.

The invention claimed is:

1. A monovalent vaccine formulation against *Vibrio cholerae* O139 comprising:
a live attenuated cholera vaccine strain;

a vaccine medium having starch, cellulose, dextrose, and yeast extract; and a phosphate buffer saline;

wherein the strain is VCUSM14P and wherein the vaccine medium comprising starch (3.25-6.75%), cellulose (2.50-4%), dextrose (18.25-24.50%), yeast extract (0.01-0.05%), and NaCl (0.05-0.15%).

2. The formulation of claim 1, wherein the formulation comprising at least 1000 mL of phosphate buffer saline at pH 7.2±0.2.

3. The formulation of claim 1, wherein the formulation is in oral liquid form.

4. A method for preparing a monovalent vaccine formulation of claim 1, wherein the method comprising:

culturing of live attenuated bacterial cells of strain in a vaccine growth medium;

recovering the bacterial cells from the culture; and suspending the recovered bacterial cells in phosphate buffer saline, wherein the strain is VCUSM14P.

5. The method of claim 4, wherein the vaccine medium comprising having starch (3.25-6.75%), cellulose (2.50-4%), dextrose (18.25-24.50%), yeast extract (0.01-0.05%), and NaCl (0.05-0.15%) in a 1000 mL of phosphate buffer saline at pH 7.2±0.2.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: VHF primer

<400> SEQUENCE: 1
gacctgtgat gtaaaggaac                                               20

<210> SEQ ID NO 2
<211> LENGTH: 20
<212> TYPE: DNA
<213> ORGANISM: Artificial Sequence
<220> FEATURE:
<223> OTHER INFORMATION: VHR primer

<400> SEQUENCE: 2
cttcatagcg ctcaacaagg                                               20

<210> SEQ ID NO 3
<211> LENGTH: 31
<212> TYPE: DNA
<213> ORGANISM: Artificial Sequence
<220> FEATURE:
<223> OTHER INFORMATION: KanFse-2F

<400> SEQUENCE: 3
agcggccggc cgcttacatg gcgatagcta g                                  31

<210> SEQ ID NO 4
<211> LENGTH: 31
<212> TYPE: DNA
<213> ORGANISM: Artificial Sequence
<220> FEATURE:
<223> OTHER INFORMATION: KanFse-R

<400> SEQUENCE: 4
ataggccggc ctcagaagaa ctcgtcaaga a                                  31

<210> SEQ ID NO 5
<211> LENGTH: 21
<212> TYPE: DNA
<213> ORGANISM: Artificial Sequence
<220> FEATURE:
<223> OTHER INFORMATION: MctxA112MS-F

<400> SEQUENCE: 5
tacagtcctc atccagatca g                                             21

<210> SEQ ID NO 6
<211> LENGTH: 21
<212> TYPE: DNA
```

-continued

```
<213> ORGANISM: Artificial Sequence
<220> FEATURE:
<223> OTHER INFORMATION: ctxBCDS-R

<400> SEQUENCE: 6
aattgccata ctaattgcgg c                                         21

<210> SEQ ID NO 7
<211> LENGTH: 21
<212> TYPE: DNA
<213> ORGANISM: Artificial Sequence
<220> FEATURE:
<223> OTHER INFORMATION: MctxA112WS-F

<400> SEQUENCE: 7
tacagtcctc atccagatga a                                         21

<210> SEQ ID NO 8
<211> LENGTH: 21
<212> TYPE: DNA
<213> ORGANISM: Artificial Sequence
<220> FEATURE:
<223> OTHER INFORMATION: ctxBCDS-R

<400> SEQUENCE: 8
aattgccata ctaattgcgg c                                         21
```